United States Patent [19]

Bernard et al.

[11] Patent Number: 5,712,169
[45] Date of Patent: Jan. 27, 1998

[54] SCREENING OF CANDIDATES FOR BIOLOGICAL HAIR CARE ACTIVITY

[75] Inventors: Bruno Bernard, Neuilly Sur Seine; Olivier Gaillard, Paris, both of France

[73] Assignee: Societe L'Oréal S.A., Paris, France

[21] Appl. No.: 678,979

[22] Filed: Jul. 12, 1996

[30] Foreign Application Priority Data

Jul. 12, 1995 [FR] France ................... 95 08465

[51] Int. Cl.$^6$ .............. G01N 33/567; A61K 49/00; A61K 7/06; C12N 5/00
[52] U.S. Cl. .............. 436/503; 436/501; 424/9.1; 424/62; 424/70.1; 424/70.6; 424/70.8; 424/70.11; 424/70.19; 424/74; 435/40.52; 435/240.2
[58] Field of Search ............. 435/6, 40.52, 240.2; 436/501, 503; 424/9.1, 62, 70.1, 70.6, 70.8, 70.11, 70.19, 74

[56] References Cited

U.S. PATENT DOCUMENTS 5,229,271  7/1993  Philpott ....................... 435/29

FOREIGN PATENT DOCUMENTS 0434319  6/1991  European Pat. Off. .

OTHER PUBLICATIONS

Developmental Biology, vol. 165, 1994 New York, N.Y., pp. 469–479.

British Journal of Dermatology, vol. 131, No. 1, Jul. 1994 Oxford, pp. 166–176.

Journal of Anatomy, vol. 185, Dec. 1994 Cambridge, pp. 135–142.

*Primary Examiner*—Bradley L. Sisson
*Attorney, Agent, or Firm*—Burns, Doane, Swecker & Mathis, L.L.P.

[57] ABSTRACT

A procedure for screening a candidate substance for biological hair care activity comprises (i) microdissecting and isolating at least one viable hair follicle and the epidermal surroundings thereof, while preserving the continuity of such at least one hair follicle and the epidermal environment thereof, but removing the adipose tissue therefrom, (ii) incubating the at least one hair follicle in a nutrient medium for a given period of time, (iii) contacting the at least one incubated hair follicle with the candidate substance for biological hair care activity, and (iv) measuring a marker of the hair care activity of the candidate substance and thence evaluating the results of such measurement in comparison with a control.

10 Claims, 2 Drawing Sheets

SCREENING OF CANDIDATES FOR BIOLOGICAL HAIR CARE ACTIVITY

This application claims priority under 35 U.S.C. §119 to French application 95-08465, filed on Jul. 12, 1995.

BACKGROUND OF THE INVENTION

1. Technical Field of the Invention

The present invention relates to the screening or testing of candidate substances, e.g., chemical compounds, species or compositions, for potential biological activity in the field of hair care.

The field of hair care especially comprehends the hair of a human individual. Accordingly, by the expression "substance potentially active in the field of hair care," or, simply, the word "substance" or "species" is/are intended any molecule or group of molecules exhibiting potential activity in the hair care field, and, in particular, any molecule or combination of molecules potentially acting on the pigmentation, survival, increasing or arresting hair growth, hair loss, or intensified growth of the hair follicles.

Per this invention, the substance or species to be tested may be used either in the molecular form thereof, or in the form of a composition comprising the molecule to be screened.

2. Description of the Prior Art

To date, the prior art has focused on two principal methods for testing a substance potentially active in the field of hair care.

The first entails conducting tests on volunteer subjects and in recording, relatively rapidly, the effects of the substance tested. This technique obviously presents many disadvantages, including, in particular, the problem of use on human beings, thereby manifestly restricting the scope of application for ethical reasons. As a result, the number and quality of the tested species are limited. Furthermore, these tests normally require extensive resources and are conducted over long periods of time. Accordingly, in most instances the test results comprise mere observations of phenotypic modifications of the hair follicle.

The second technique known to the prior art is described in EP-0-434,319. This method entails a step in which the hair follicle is dissected and in which, beginning with a skin sample containing follicles, the hair shaft is cut below the dermal/epidermal junction, then the follicle is isolated from the surrounding skin without damaging the root.

A modification of this technique has been suggested by Williams and Stenn, *Dev. Biol.*, 165, 469–479 (1994), comprising preliminarily cutting the biopsy into vertical strips 1 mm thick, then conducting a dissection according to the procedure described in EP-0-434,319 by extracting the follicle from its environment using tweezers.

Texts featuring hair and its biology contain complete information regarding the full composition of the hair follicle. Exemplary is C. Zviak, *Sciences des traitements capillaires*, Edition Masson (1987).

The in vitro test methods described above do not permit the study of hair follicle reactions in its epidermal environment with respect to the substance to be screened. Indeed, in each of these techniques the biopsy is first cut into sections below the dermal/epidermal interface, thereby separating the hair follicle from its epidermal surroundings.

By the term "epidermal environment" or "epidermal surroundings" is intended the upper layer of the skin (epidermis) at the anastomosis of the pilosebaceous duct enclosing the deep portion of the hair shaft. The epidermis is invaginated along the duct, thereby forming the first elements of the epithelial sheaths in close contact with the hair shaft.

This separation of the hair shaft from its epidermal environment presents numerous difficulties. For example, in the in vitro methods known to the prior art, the lack of close contact between the follicle and its epidermal surroundings during dissection causes mechanical stresses on the follicle resulting from the stresses produced by dissection, these forces impairing the ability to obtain an intact follicle, and, more particularly, an intact root. Thus, the probability of obtaining an intact root, a precondition for the survival of the follicle in vitro, is slight. As a result, the effectiveness with which an intact root can be obtained is reduced.

In addition, in the in vitro models according to prior art, the lack of close contact between the follicle and its epidermal environment distances these models from reality. Indeed, these models do not incorporate the parameters linked to the close contact existing between the follicle and its epidermal environment, these parameters not being applicable even before dissection has begun. Accordingly, the results obtained from the study of a substance or species potentially active in the hair care field using these models do not take into account the interactions between the follicle and its epidermal environment, and thus do not conform to reality.

It is known, moreover, that the hair follicle develops through a hair cycle which is normally circumscribed by the three basic phases comprising same.

The first phase is an active, so-called anagenetic phase lasting several years. During this phase, the follicle penetrates deeply into the dermis. Intense activity is observed in the root cells, which become differentiated in order to produce a hair.

The second, so-called catagenetic phase is a regressive phase lasting approximately three weeks, during which mitosis stops and the hair ceases to grow.

During this phase, the follicle ascends toward the upper end of the dermis, while the dermal papilla remains in the deepest layers, with formation and elongation, at the base of the root, of an epithelial column, at the lower end of which the dermal papilla is located.

The third, or telogenetic phase is a resting or quiescent phase lasting approximately three months. During this phase, the papilla produces a secondary germ which, by cell division, will lengthen and form a new root, thereby permitting a new anagenetic phase to commence, while the previous dead hair remains in place for several months and finally falls out, pushed outside its sheath by the nascent hair.

It may prove significant to have the ability to screen a potentially active agent in the field of hair care based on the phase of the cycle through which the hair follicle is passing. Now, an additional problem common to both in vitro methods according to prior art resides in the fact that it is not possible to select the hair follicle as a function of the phase of development thereof. The two known techniques according to the prior art entail "blind" phases which do not permit a preliminary selection of any particular follicle in accordance with the phase of the cycle it is traversing, the exact identification of phase normally occurring by observation of the state of the follicle (non-visible portion) and not by the state of the hair (visible portion).

SUMMARY OF THE INVENTION

Accordingly, a major object of the present invention is the provision of an improved technique for the screening of potentially active agents in the field of hair care, which improved technique avoids or conspicuously ameliorates the above disadvantages and drawbacks to date characterizing the state of this art.

Briefly, the present invention features methodology for screening or testing a potentially active agent or species in the field of hair care, comprising:

(i) preparing, via microdissection, at least one viable hair follicle and its epidermal environment, in which continuity is preserved, but in which the adipose tissue is removed;

(ii) incubating said at least one hair follicle in appropriate culture medium for a sufficient length of time;

(iii) then contacting said at least one hair follicle with a substance potentially active in the field of hair care; and (iv) assessing the activity of said tested substance vis-a-vis a marker therefor, and evaluating the results thereof in comparison with a control.

Figure 1:
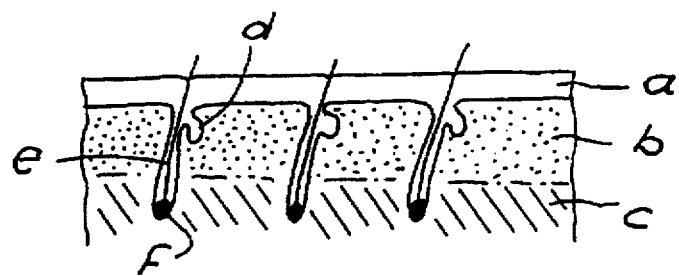
FIG. 1 is a schematic illustration of steps (i) and (ii) of the procedure according to the invention, wherein a represents the epidermis, b the dermis, c the adipose tissue, d the sebaceous gland, e the hair shaft, f the dermal papilla, g the nutrient medium, and h the substrate.
Figure 1:
Figure 1:
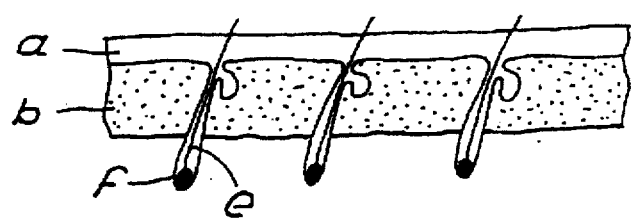
Figure 1:
Figure 1:
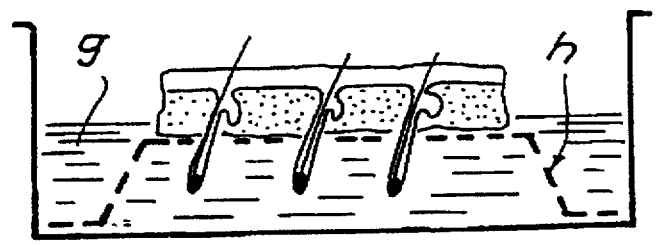
Figure 1:
Figure 1:
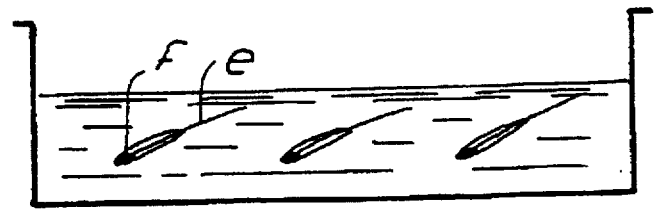

DETAILED DESCRIPTION OF BEST MODE AND SPECIFIC/PREFERRED EMBODIMENTS OF THE INVENTION

More particularly according to the present invention, the expression "preserved continuity of the hair follicle and of its epidermal environment" connotes that the hair follicle and its epidermal environment are not separated by microdissection. Furthermore, in the procedure of this invention, the hair follicle obtained following step (i) may preserve all or a portion of its dermal environment, in addition to its epidermal surroundings (see FIG. 1).

According to the invention, the term "hair follicle" connotes a unit comprising a dermal papilla, a root, and a hair shaft enclosed in its sheaths. This follicle normally corresponds to a hair, a cilium, or an eyebrow.

The hair follicle may also incorporate some of its attachments or appendages, such as the sebaceous gland in particular.

The procedure according to the invention utilizes a skin biopsy, namely, a sample of human or animal skin containing at least one hair follicle.

A sample of skin excised from the legs or scalp is preferred, especially from the scalp.

The viable hair follicle must have an undamaged root.

A viable in vitro intact hair follicle is obtained from the skin biopsy by removing the adipose tissue therefrom.

Any conventional technique permitting removal of the adipose tissue from the biopsy can be employed in the procedure of the invention.

In particular, the adipose tissue is removed using microsurgical instruments, such as a microforceps or a scalpel. A microforceps is preferably used.

To ensure to the greatest possible extent that the root is undamaged, the dissection is carried out under a binocular magnifying glass with adequate lighting.

Using the instrument selected, the adipose tissue is normally removed, beginning by first pulling away the portions most distant from the skin surface. Complete dissection is achieved by pulling away all of the adipose tissue, by removing it gradually while ascending toward the skin surface and by separating it cautiously from the hair follicle.

The procedure according to the invention permits isolating the hair follicle directly, since the follicle is stripped of the adipose tissue surrounding it.

Thus, at the end of the first step, selection may be made based on the state of development of the follicle. In this manner, it is possible to readily isolate hair follicles in the anagenetic, catagenetic, or telogenetic phase.

Moreover, in the case of pigmentation, the procedure permits monitoring the progress of a potentially active substance useful for the coloration or recoloration of the hair within the follicle, and to simultaneously compare this progress with that occurring in its epidermal environment.

It should be appreciated that the requirements of the screening procedure may dictate that only one portion of the hair follicle is needed. Once the hair follicle and its epidermal environment are isolated, the hair shaft can be cut at the desired level, in order to collect only the elements required for analysis.

Accordingly, the procedure according to the invention presents the advantage of permitting the selection of all or a portion of the hair follicle, as desired, optionally accompanied by its epidermal environment.

In a preferred embodiment of the invention, after step (i), the procedure may entail an additional step in which the hair follicle is separated from its epidermal, and optionally dermal environment. In this manner, it is possible to cut the hair shaft to separate the bulb from its epidermal, and optionally dermal, environment. FIG. 1 illustrates this operating technique.

After step (i), the hair follicle, whether or not accompanied by its epidermal environment, is incubated in a suitable culture medium which may contain the substance to be tested. The substance to be tested may of course be added to the incubation medium at any instant, namely, before or after the hair follicle is contacted with the incubation medium. This medium is a nutrient medium including at least the constituents required to maintain survival of the hair follicle. It may obviously contain any other constituent necessary, for example, for hair follicle growth.

Exemplary such culture media are well known to this art, and include modified Dulbecco MEM medium, the Williams E medium, the F12 medium, the HAM medium, and RPM1140, marketed by Gibco-BRL, Biomed, Boehringer, or Sigma. The Williams E medium is preferred.

A substrate may be present in the culture medium to maintain the hair follicle and its accompanying epidermal, and optionally dermal environment, at the surface thereof (see FIG. 1).

In general, the incubation time is governed by the time required for the hair follicle to respond to the potentially active hair care substance with which it is contacted, namely, the time required to observe a change in the level of expression of the marker of the activity of the tested substance being quantitatively analyzed.

This incubation time may range from several seconds to several days. For informational purposes, the incubation time normally ranges from 10 seconds to 30 days, and preferably from 1 to 96 hours.

Exemplary markers include protein, DNA, RNA, organelle, ion, metal, amino acid, lipid, and liposoluble compound. It should be appreciated that the marker of the activity of the substance potentially active in the hair field may be the appearance, e.g., the length, of the follicle, and, more especially, of the hair shaft.

The activity of the substance to be tested is thus represented by the variation of the marker of said activity selected for measurement. This variation may, therefore, represent a modification of the quantity, concentration, or distribution of the marker, or, again, a modification of follicle appearance.

To this end, the procedure according to the invention includes a step entailing measurement of the marker of the activity of the substance screened.

After incubation, this measurement may be made directly on the culture medium as regards the elements excreted by the cell, in the hair follicle as regards the elements not excreted, or again, directly on the hair follicle to evaluate a change in the appearance of this follicle, such as length of the shaft.

Accordingly, and more especially in the event that the element or constituent sought is not excreted, an additional step may be carried out prior to measurement, during which the hair follicle is ground, to increase accessibility of the marker of the activity of the tested substance to be measured.

Of course, whatever the embodiment of the procedure according to the invention, any quantitative analysis technique known to this art may be employed.

Exemplary techniques for quantitative analysis of proteins or nucleic acids include those based on colorimetry, electrophoresis, reverse transcriptase and amplification via chain polymerization, mass spectrography, chromatography (gas or plate), immunobiological methods, or optical or electron microscopy for measuring the quantity of an organelle.

The results of the quantitative analysis cannot themselves be used directly. The results are useful only when compared to the results of the same quantitative analysis carried out under the same conditions, but in the absence of any contacting of the hair follicle scraped away with the substance to be tested.

Accordingly, the process according to the invention includes a step during which the results of the quantitative analysis are evaluated in comparison with a control.

In the hair field, the potentially active substances or species to be tested are normally associated with a change in the condition of the hair of the subject, and preferably the present or future condition thereof.

In general, the substances to be tested may affect the color, density, quantity, or quality of the hair follicles. These substances may, for example, affect the slowing or arresting, stoppage of growth, loss, maintaining, or increased or intensified growth of the hair follicles.

Thus, the present invention permits screening potentially active substance in the hair field which affect maintaining, slowing or arresting, stoppage of growth, loss, coloration, or the intensified growth of hair follicles.

Preferably, the procedure according to the invention permits the screening of substances which may have an effect on the slowing, stoppage of growth, loss, or coloration of hair follicles.

Moreover, the procedure according to the invention allows evaluation of the activity of a substance which may be used for preparing a cosmetic composition or drug useful for treating alopecia.

The procedure according to the invention is also useful for evaluating the efficacy of a given treatment of a particular test subject.

In order to further illustrate the present invention and the advantages thereof, the following specific example is given, it being understood that same is intended only as illustrative and in nowise limitative.

EXAMPLE

A narrow strip of scalp was excised from a scalp biopsy using a scalpel. By means of a microforceps, the adipose tissue surrounding the hair follicles was removed, while avoiding any damage to the hair roots. Under a microscope, a follicle was cut with a scalpel to separate it from its epidermal and dermal environment.

Figure 2:
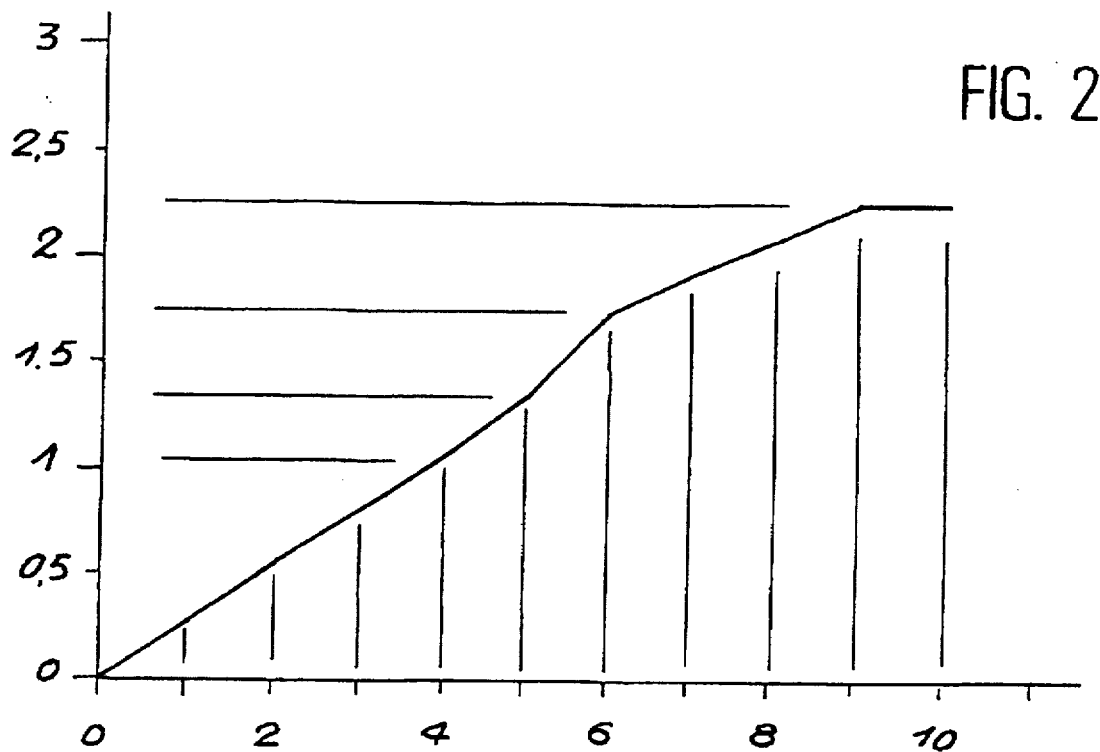
FIG. 2 is a graph of the growth curve of the hair follicles (expressed in nanometers) as a function of culturing time (expressed in number of days).
Figure 3:
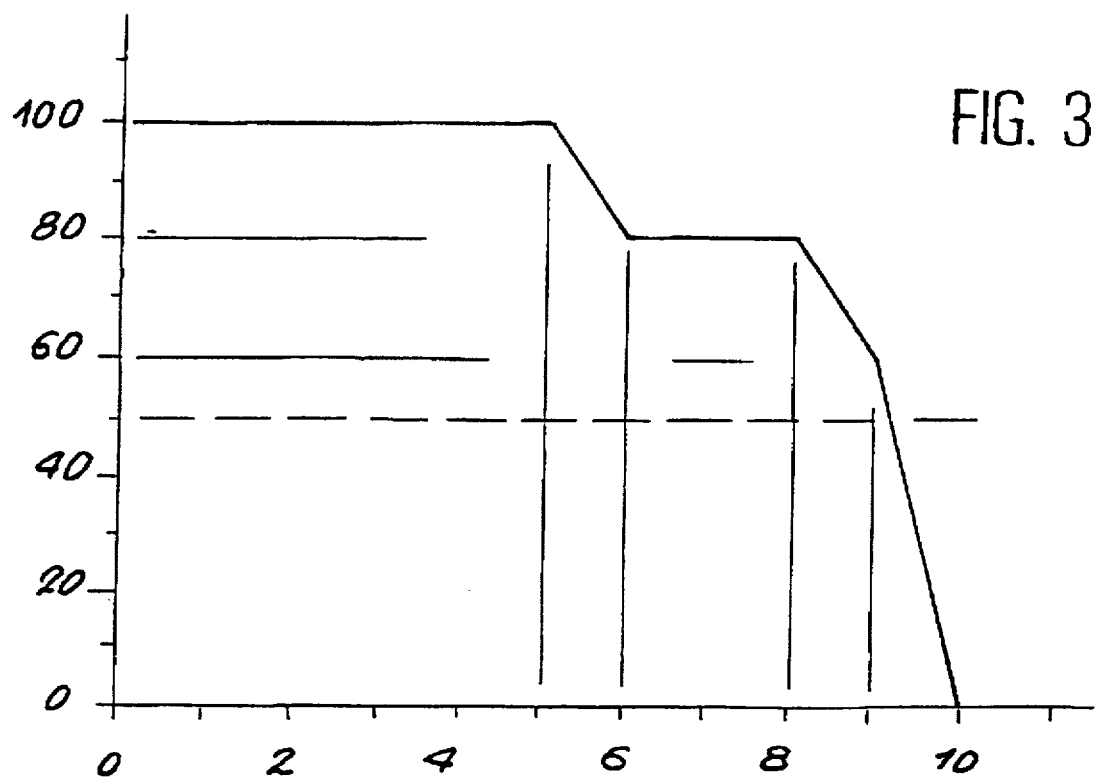
FIG. 3 is a curve indicating the percentage of survival of the hair follicles as a function of culturing time (expressed in number of days).

The fragment thus produced was maintained cultured in Williams E medium at 37° in a moist atmosphere in the presence of 5% $CO_2$ FIG. 2 indicates that the fragment thus obtained and maintained in histoculture lengthened steadily at a rate of approximately 0.3 mm per day, which is comparable to the in vivo rate of lengthening of the hair. This growth was observed for 10 days, with a survival rate of 100% at 5 days and a survival rate remaining greater than 50% at 9 days (FIG. 3). This remarkable survival rate can be attributed to the fact that the dissection technique permits the selection of intact hair follicles and, accordingly, optimization of the histoculture success rate.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An improved method for identifying a candidate substance which exhibits bioactivity on hair, wherein said bioactivity is selected from the group consisting of promoting hair growth, maintaining hair growth, increasing hair growth, arresting hair growth, terminating hair growth, affecting hair loss, affecting hair coloration or pigmentation, and exhibiting cosmetic activity, wherein the improvement comprises identifying a compound exhibiting at least one of said bioactivities on hair by a method comprising the following combination of steps:

(i) microdissecting and isolating at least one viable hair follicle comprising a dermal papilla, a root and a hair shaft enclosed within its sheaths, under conditions that maintain the epidermal surroundings thereof, wherein epidermal surroundings refer to the upper layer of the skin (epidermis) at the anastomosis of the pilosebaceous duct that encloses the deep portion of the hair shaft;

(ii) removing the adipose tissue therefrom;

(iii) incubating said at least one hair follicle in a nutrient medium;

(iv) contacting said at least one incubated hair follicle with said candidate substance to determine whether it exhibits at least one of said bioactivities on hair; and (v) evaluating the efficacy of said candidate substance as a hair bioaffecting agent based on its relative ability to affect one or more of said bioactivities in comparison to a control composition containing at least one viable hair follicle isolated and cultured under identical conditions except for the absence of said candidate substance.

2. The method of claim 1, wherein said nutrient medium of step (iii) contains at least one constituent that is required for growth of said at least one viable hair follicle.

3. The method as defined by claim 1, wherein in said step (iii), the incubation time ranges from as low as 10 seconds to the maximum amount of time wherein a sufficient number of said at least one hair follicle remain viable in said nutrient medium to permit the identification of a candidate substance that exhibits at least one of said bioactivities on hair.

4. The method as defined by claim 1, wherein said at least one viable hair follicle is isolated in its anagenetic phase.

5. The method as defined by claim 1, wherein said at least one viable hair follicle is isolated in its catagenetic phase.

6. The method as defined by claim 1, wherein said at least one viable hair follicle is isolated in its telogenetic phase.

7. The method as defined by claim 1, which is used to identify a substance suitable for the treatment of alopecia.

8. The method as defined by claim 1, wherein said at least one microdissected and isolated at least one viable hair follicle comprises a human or animal skin biopsy sample.

9. The method as defined by claim 8, wherein in (iv) adipose tissue is removed from said skin biopsy sample beginning at the portion most distance from the skin surface and ascending gradually toward the skin surface.

10. The method as defined by claim 9, wherein the adipose tissue is removed using a microsurgical instrument.

* * * * *